United States Patent
Randolph et al.

(10) Patent No.: US 6,413,897 B1
(45) Date of Patent: Jul. 2, 2002

(54) METHOD FOR REGENERATING AN ALKYLATION CATALYST

(75) Inventors: Bruce B. Randolph; Marvin M. Johnson, both of Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/528,977

(22) Filed: Mar. 21, 2000

(51) Int. Cl.[7] .................. B01J 20/34; B01J 38/50; C07C 2/58; C07C 7/00; C07C 7/17
(52) U.S. Cl. .................. 502/31; 502/29; 502/34
(58) Field of Search .................. 502/29, 31, 34; 585/724, 802, 857

(56) References Cited

U.S. PATENT DOCUMENTS

| | | | |
|---|---|---|---|
| 3,886,220 A | 5/1975 | Carter | 260/653.6 |
| 4,243,830 A | 1/1981 | Carson | 585/717 |
| 5,264,647 A * | 11/1993 | Eastman et al. | 585/724 |
| 5,461,183 A | 10/1995 | Del Rossi et al. | 585/802 |
| 5,723,715 A * | 3/1998 | Randolph et al. | 585/724 |
| 5,753,575 A | 5/1998 | Anderson et al. | 502/31 |

* cited by examiner

Primary Examiner—Steven P. Griffin
Assistant Examiner—Jonas N. Strickland
(74) Attorney, Agent, or Firm—Jeffrey R. Anderson

(57) ABSTRACT

Disclosed is an alkylation process which utilizes a catalyst containing hydrogen fluoride, and, optionally, a volatility reducing additive, as an alkylation catalyst. The process provides for the regeneration of an alkylation catalyst having ASO, and, optionally, a volatility reducing additive, therein by separating HF from the ASO and the optional volatility reducing additive components using an upwardly flowing gas containing an isoparaffin and/or an olefin. Where a volatility reducing additive is used, the ASO and volatility reducing additive are thereafter separated to provide a volatility reducing additive which is substantially free of ASO.

21 Claims, 1 Drawing Sheet

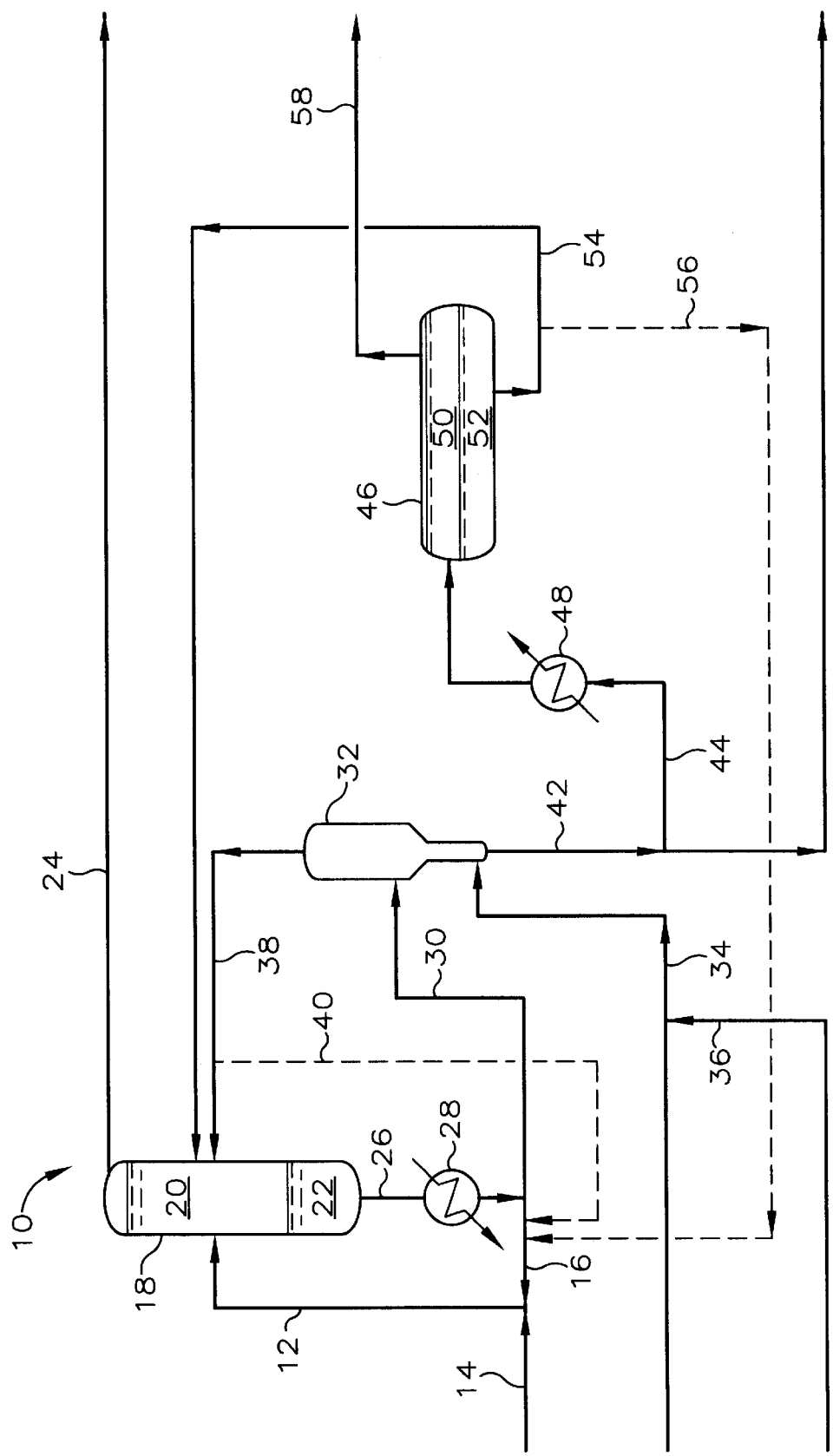

METHOD FOR REGENERATING AN ALKYLATION CATALYST

The present invention relates to the alkylation of olefinic hydrocarbons with isoparaffin hydrocarbons in the presence of an alkylation catalyst mixture comprising hydrofluoric acid (HF) and, optionally, a volatility reducing additive. More particularly, the invention relates to the removal of HF from an alkylation catalyst mixture by contact with a gas stream comprising isoparaffins and/or olefins in a stripping column.

BACKGROUND OF THE INVENTION

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the mixture to separate the catalyst from the hydrocarbons and further separating the alkylation reactor effluent, for example, by fractionation, to recover the separate product streams. Normally, the alkylation reactor effluent of the alkylation process contains hydrocarbons having five to sixteen carbon atoms per molecule, preferably seven to nine carbon atoms per molecule. In order to have the highest quality gasoline blending stock, it is preferred for the alkylate hydrocarbons formed in the alkylation process to be highly branched and contain seven to nine carbon atoms per molecule.

Recent efforts to improve conventional hydrogen fluoride catalyzed alkylation processes have resulted in the development of new catalyst compositions that contain hydrogen fluoride and a volatility reducing additive. These new catalyst compositions have been found to be quite effective as alkylation catalysts and provide many other favorable benefits.

Regeneration of an alkylation catalyst mixture containing HF, acid soluble oil (ASO), and, optionally, a volatility reducing additive generally includes stripping HF from the catalyst mixture using a combination of elevated temperatures and an isoparaffin stripping gas, for combination of the stripped HF with the alkylation catalyst mixture. The bottoms stream from such a stripper (commonly referred to as a re-run column) contains the ASO and, if present, the volatility reducing additive. Where a volatility reducing additive is used, the re-run column bottoms stream is then separated into an ASO stream and a volatility reducing additive stream, and the volatility reducing additive stream is combined with the alkylation catalyst. On occasion, in the operation of such a re-run column, adequate heating capacity and/or stripping gas (isoparaffin) is not available in order to adequately remove HF from the bottoms stream. Elevated levels of HF in the bottoms stream requires neutralization and a costly loss of such HF, and can cause less efficient separation of ASO from the volatility reducing additive. Therefore, development of an efficient process for reducing the concentration of HF in the bottoms stream of an isoparaffin re-run column used in an alkylation process would be a significant contribution to the art.

BRIEF SUMMARY OF THE INVENTION

It is an object of the present invention to provide a novel method for regenerating an alkylation catalyst containing HF, ASO and, optionally, a volatility reducing additive.

It is a further object of this invention to provide an improved method for removing HF from a regenerable alkylation catalyst containing HF, ASO and, optionally, a volatility reducing additive.

A still further object of this invention is to provide a method for reducing the concentration of HF present in the bottoms stream of an alkylation process system re-run column.

A yet further object of this invention is to provide a method for increasing the ASO recovery from an alkylation process system re-run column bottoms stream.

The present invention is a method for regenerating an alkylation catalyst mixture used in an alkylation process system comprising the steps of:

alkylating a first olefin with a first isoparaffin in the presence of an alkylation catalyst mixture comprising HF in an alkylation reaction zone thereby producing an alkylate product and an ASO reaction by-product;

passing an alkylation reaction zone effluent comprising the alkylate product, the ASO reaction by-product and the alkylation catalyst mixture from the alkylation reaction zone to a separation zone for separating the alkylation reaction zone effluent into a hydrocarbon phase comprising the alkylate product, and an alkylation catalyst mixture phase comprising the alkylation catalyst mixture and the ASO reaction by-product;

passing at least a portion of the alkylation catalyst mixture phase to a re-run column for contact with an upwardly flowing gas stream comprising a second olefin and a second isoparaffin to provide a re-run column bottoms stream comprising at least a portion of the ASO reaction by-product, and a re-run column overhead stream comprising HF, at least a portion of the gas stream and an organic fluoride.

Other objects and advantages will become apparent from the detailed description and the appended claims.

BRIEF DESCRIPTION OF THE OF THE DRAWING

The FIGURE is a schematic flow diagram presenting an embodiment of the present invention.

DETAILED DESCRIPTION OF THE INVENTION

In accordance with the present invention, a first olefin can be alkylated with a first isoparaffin in the presence of an alkylation catalyst mixture comprising, consisting of, or consisting essentially of HF in an alkylation reaction zone to thereby produce an alkylation reaction zone effluent comprising, consisting of, or consisting essentially of an alkylate product, an ASO reaction by-product, and the alkylation catalyst mixture.

In another embodiment, the alkylation catalyst mixture comprises, consists of, or consists essentially of HF and a volatility reducing additive.

The first olefin can be any olefin suitable for alkylation. Preferably, the first olefin comprises, consists of, or consists essentially of at least one olefinic hydrocarbon having at least 3 carbon atoms per molecule and, more preferably, 3 to 4 carbon atoms per molecule. The first isoparaffin preferably comprises, consists of, or consists essentially of at least one isoparaffinic hydrocarbon having at least 4 carbon atoms per molecule, and, more preferably, 4 to 5 carbon atoms per molecule. Most preferably, the first olefin is selected from the group consisting of propylene, butene-1, isobutene, 2-butenes, methyl butenes, pentenes and combinations of any two or more thereof; and the first isoparaffin is selected from the group consisting of isobutane, isopentane, and combinations thereof.

The volatility reducing additive can be any compound effective in reducing the volatility of a mixture resulting from the addition of the volatility reducing additive to a hydrofluoric acid. More particularly, the volatility reducing additive can be a compound selected from the group consisting of sulfone, ammonia, methylamines, ethylamines, propylamines, butylamines, pentylamines, pyridine, alkylpyridines, melamine, hexamethylene-tetramine and the like, and combinations of any two or more thereof.

The sulfones suitable for use in this invention are the sulfones of the general formula

wherein R and $R^1$ are monovalent hydrocarbon alkyl or aryl substituents, each containing from 1 to 8 carbon atoms, and wherein R and $R^1$ can be the same or different. Examples of suitable sulfones include, but are not limited to, dimethylsulfone, di-n-propylsulfone, diphenylsulfone, ethylmethylsulfone and alicyclic sulfones wherein the $SO_2$ group is bonded to a hydrocarbon ring. In such a case, R and $R^1$ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures of any two or more thereof. The most preferred volatility reducing additive is sulfolane.

As used within this description and in the appended claims, the term "acid soluble oil", or "ASO", means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of conjunct Polymers", pages 150–160, Volume 8, Number 1, (January 1963) by Miron and Lee. This article is incorporated herein by reference.

The physical properties of ASO depend upon the particular hydrocarbon feed processed, the catalyst utilized in the process, feed contaminants such as hydrogen sulfide, butadiene, oxygenates and other compounds, and the alkylation process reaction conditions.

The ASO reaction by-product can be further generally characterized as having a specific gravity, with water at 60° F. as the reference, in the range of from about 0.8 to about 1.0, an average molecular weight in the range of from about 250 to about 350, and a bromine number in the range of from about 40 to about 350. The boiling temperature of the ASO reaction by-product can range from an initial boiling point of about 200° F. to an end-point of about 1100° F.

The alkylation reaction zone effluent can be passed from the alkylation reaction zone to a separation zone wherein a phase separation occurs. The phase separation produces a hydrocarbon phase. The hydrocarbon phase can comprise, consist of, or consist essentially of the alkylate product, unreacted isoparaffins, and fluoroalkanes and can be removed from the separation zone for further downstream processing.

The phase separation in the separation zone also produces an alkylation catalyst mixture phase which can be used, at least in part, as the alkylation catalyst mixture. The alkylation catalyst mixture phase comprises, consists of, or consists essentially of the alkylation catalyst mixture and at least a portion of the ASO reaction by-product produced.

To regenerate the alkylation catalyst mixture, at least a portion of the alkylation catalyst mixture phase is passed to a re-run column, which provides means for separating the alkylation catalyst mixture phase into a re-run column bottoms stream and a re-run column overhead stream. The at least a portion of the alkylation catalyst mixture phase can also be referred to as a slip stream. The remaining portion of the alkylation catalyst mixture phase is recycled to the alkylation reaction zone for use as the alkylation catalyst mixture. The slip stream of the alkylation catalyst mixture phase is contacted, within the re-run column, with an upwardly flowing gas stream comprising a hydrocarbon selected from the group consisting of a second olefin, a second isoparaffin, and combinations thereof, to provide the re-run column bottoms stream comprising, consisting of, or consisting essentially of at least a portion of the ASO reaction by-product and, where a volatility reducing additive is present in the alkylation catalyst mixture, the re-run column bottoms stream comprises, consists of, or consists essentially of at least a portion of the ASO reaction by-product and at least a portion of the volatility reducing additive. Also provided is the re-run column overhead stream comprising, consisting of, or consisting essentially of HF, at least a portion of the gas stream, and at least one organic fluoride. The organic fluoride typically has 3 to 8 carbon atoms per molecule.

Preferably, at least about 90 weight percent of the HF contained in the slip stream passed to the re-run column passes overhead in the re-run column overhead stream, more preferably at least about 95 weight percent, and most preferably at least 98 weight percent.

A portion of the first olefin can be used as the second olefin and a portion of the first isoparaffin can be used as the second isoparaffin.

The second olefin comprises, consists of, or consists essentially of at least one olefinic hydrocarbon having at least 3 carbon atoms per molecule, and, more preferably, 3 to 5 carbon atoms per molecule. The second isoparaffin preferably comprises, consists of, or consists essentially of at least one isoparaffinic hydrocarbon having at least 4 carbon atoms per molecule, and, more preferably, 4 to 5 carbon atoms per molecule. Most preferably, the second olefin is selected from the group consisting of propylene, butene-1, isobutene, 2-butenes, methyl butenes, pentenes and combinations of any two or more thereof; and the second isoparaffin is selected from the group consisting of isobutane, isopentane, and combinations thereof.

At least a portion of the re-run column overhead stream can be added to the remaining portion of the alkylation catalyst mixture phase recycled to the alkylation reaction zone, or, added to the alkylation catalyst mixture phase in the separation zone prior to alkylating the first olefin with the first isoparaffin, for use as part of the alkylation catalyst mixture. The organic fluorides present in the portion of the re-run column overhead stream added to the alkylation catalyst mixture and contacted with the first isoparaffin in the alkylation reaction zone are believed to be alkylated, thus producing alkylate product and HF.

The weight ratio of the second isoparaffin to the second olefin present in the upwardly flowing gas stream is preferably in the range of from about 0.01 to about 100, more preferably from about 0.1 to about 10, and most preferably from 0.25 to 5.

The re-run column bottoms stream is then passed downstream for further processing of the ASO.

Where a volatility reducing additive is present in the alkylation catalyst mixture, the re-run column bottoms stream is passed to a separator or decanter and allowed to separate into an upper phase and a lower phase. The upper phase comprises a major portion of the at least a portion of the ASO reaction by-product and the lower phase comprises a major portion of the at least a portion of the volatility reducing additive. At least a portion of the lower phase can be added to the remaining portion of the alkylation catalyst mixture phase recycled to the alkylation reaction zone, or added to the alkylation catalyst mixture phase in the separation zone prior to alkylating the first olefin with the first isoparaffin, for use as part of the alkylation catalyst mixture.

Now referring to the FIGURE, there is depicted by schematic representation an alkylation process system 10. A hydrocarbon mixture comprising, consisting of, or consisting essentially of at least one olefin and at least one isoparaffin is introduced into riser reactor 12, which defines an alkylation reaction zone, via conduit 14. The hydrocarbon mixture is contacted with an alkylation catalyst mixture (described above). The alkylation catalyst mixture is introduced to riser reactor 12 via conduit 16. The admixture of the hydrocarbon mixture and the alkylation catalyst mixture passes through the alkylation reaction zone defined by riser reactor 12 wherein a reaction takes place in which the olefins of the hydrocarbon mixture react with isoparaffins of the hydrocarbon mixture to produce an alkylate product and an ASO reaction by-product. An alkylation reaction zone effluent comprising, consisting of, or consisting essentially of the alkylate product, the ASO reaction by-product and the alkylation catalyst mixture passes to a settler vessel 18, which defines a separation zone for separating the alkylate product from the alkylation catalyst mixture to produce a hydrocarbon phase 20 comprising, consisting of, or consisting essentially of the alkylate product, and an alkylation catalyst mixture phase 22 comprising, consisting of, or consisting essentially of the alkylation catalyst mixture and at least a portion (and preferably a substantial portion) of the ASO reaction by-product. The separated hydrocarbon phase 20 passes to downstream processing via conduit 24. The separated alkylation catalyst mixture phase 22 can be recycled to riser reactor 12 via conduits 26 and 16 for reuse as the alkylation catalyst mixture. Interposed in conduit 26 is catalyst cooler 28, which defines a heat transfer zone for exchanging heat from separated alkylation catalyst mixture phase 22 to a heat transfer fluid such as water.

In order to regenerate the alkylation catalyst mixture phase, at least a portion (a slip stream) of the alkylation catalyst mixture phase 22 passes via conduit 30 to re-run column 32. Re-run column 32 provides means for stripping HF from the slip stream of the alkylation catalyst mixture phase 22 charged thereto and to provide a re-run column bottoms stream and a re-run column overhead stream. Introduced into re-run column 32 via conduit 34 is a vaporous isoparaffin which provides energy for separating the slip stream into the re-run column overhead stream and the re-run column bottoms stream, and, more specifically, for stripping HF from the slip stream. Also introduced into re-run column 32 via conduits 36 and 34 is a vaporous olefin which reacts with HF to form an organic fluoride which passes overhead in the re-run column overhead stream. The re-run column overhead stream passes from re-run column 32 via conduit 38 to settler vessel 18, or passes via conduits 38, 40 and 16 to riser reactor 12. The re-run column bottoms stream passes via conduit 42 downstream for processing of the ASO.

Where the alkylation catalyst mixture contains a volatility reducing additive, the re-run column bottoms stream passes via conduits 42 and 44 to a phase separator or decanter 46. Interposed in conduit 44 is heat exchanger 48, which provides for cooling of the re-run column bottoms stream by indirect heat exchange prior to feeding the re-run column bottoms stream to decanter 46. Decanter 46 defines a separation zone and provides for the separation of the cooled re-run column bottoms stream into an upper phase 50 and a lower phase 52. The upper phase 50 comprises a major portion of the at least a portion of the ASO reaction by-product and the lower phase 52 comprises a major portion of the at least a portion of the volatility reducing additive. Lower phase 52 passes from decanter 46 through conduit 54 to settler vessel 18 wherein it is recombined with alkylation catalyst mixture phase 22 for reuse as a component of the alkylation catalyst mixture, or passes via conduits 54, 56, and 16 to riser reactor 12. Upper phase 50 passes from decanter 46 via conduit 58 downstream for processing of the ASO.

The following examples demonstrate the advantages of the present invention. These examples are for illustration purposes only and they are not intended to limit the invention as set out in the specification and the appended claims.

EXAMPLE I

This example illustrates the reaction of olefins with HF in an HF, ASO, sulfolane and water containing mixture to form organic fluorides, thus reducing the HF concentration of the mixture.

Run 1

A 53.5 g quantity of a hydrocarbon feed, having a composition as presented in Table 1, was mixed with 56.3 g of an acid mixture representative of an alkylation stripping vessel bottoms stream containing 22.9 wt. % HF, 28.1 wt. % ASO, 44.5 wt. % sulfolane and 4.4 wt. % water. The combined mixture was stirred at a rate of 1,500 rpm at a contact temperature ranging from 154° F. to 164° F. After a time period of 5 minutes the hydrocarbon and acid phases were separated and the hydrocarbon phase was analyzed by gas chromatography. Test data results are summarized in Table 2. The wt. % HF in the acid phase was determined by the following method.

The acid was collected in a monel sample cylinder and weighed. A 251.37 g quantity of 0.333N NaOH was added to an erlenmyer flask, fitted with a rubber stopper through which was run ⅛" monet tubing. The tubing length inside the flask was adjusted so that the end of the tubing was below the liquid level of the NaOH solution. A few drops of phenolphthalein was added to give a pink color.

The weighed cylinder was attached to the tubing and a small portion (12.5 g) was added to the NaOH solution slowly, until the pink color disappeared. Three separate portions of this solution were then removed (4.59 g, 4.53 g, and 4.62 g, respectively) and each were titrated to the phenolphthalein end point (first visible evidence of pink color that subsists for >30 seconds) with 6.56 mL, 6.41 mL, and 6.60 mL of 0.1000N NaOH, respectively.

The calculated HF wt. %'s from these titrations were averaged and are summarized in Table 2.

Run 2

A 66.9 g quantity of a hydrocarbon feed, having a composition as presented in Table 1, was mixed with 64.8 g of an acid mixture representative of an alkylation stripping vessel bottoms stream containing 28.2 wt. % HF, 29.7 wt. % ASO, 37.6 wt. % sulfolane and 4.4 wt. % water. The combined mixture was stirred at a rate of 1,500 rpm at a contact temperature ranging from 287° F. to 323° F. After a time period of 60 minutes the hydrocarbon and acid phases were separated and the hydrocarbon phase was analyzed by gas chromatography. Test data results are summarized in Table 2. The wt. % HF in the acid phase was determined by the following method.

The acid was collected in a monel sample cylinder and weighed. A 251.84 g quantity of 0.333N NaOH was added to an erlenmyer flask, fitted with a rubber stopper through which was run 1/8" monel tubing. The tubing length inside the flask was adjusted so that the end of the tubing was below the liquid level of the NaOH solution. A few drops of phenolphthalein was added to give a pink color.

The weighed cylinder was attached to the tubing and a small portion (11.6 g) was added to the NaOH solution slowly, until the pink color disappeared. Three separate portions of this solution were then removed (3.80 g, 3.81 g, and 3.72 g, respectively) and each were titrated to the phenolphthalein end point (first visible evidence of pink color that subsists for >30 seconds) with 4.65 mL, 4.64 mL, and 4.58 mL of 0.1000N NaOH, respectively.

The calculated HF wt. %'s from these titrations were averaged and are summarized in Table 2.

TABLE 1

Hydrocarbon Feed Composition

| Paraffins | Weight % | Olefins | Weight % |
|---|---|---|---|
| $C_3$ | 5.73 | C3= | 19.12 |
| $iC_4$ | 18.96 | iC4= | 13.01 |
| $n-C_4$ | 5.77 | 1C4= | 9.74 |
| $i-C_5$ | 3.57 | t-2C4= | 12.35 |
| $n-C_5$ | 0.07 | c-2C4= | 9.29 |
| Total Paraffins | 34.10 | 3MB1 | 0.66 |
| | | 1C5 | 0.40 |
| | | 2MB1 | 0.73 |
| | | t-2C5= | 0.22 |
| | | c-2C5= | 0.09 |
| | | 2MB2 | 0.16 |
| | | Total Olefins | 65.77 |
| $C_6+$ | | | 0.13 wt. % |
| Total Paraffins plus olefins + $C_6+$ | | | 100.00 |

TABLE 2

| | Run 1 | Run 2 |
|---|---|---|
| Hydrocarbon Phase Component, wt. % | | |
| $C_3F$ | 1.77 | 10.95 |
| $C_4F$ | 14.38 | 7.39 |
| $C_5F$ | 0.99 | 0.50 |
| $C_6F$ | — | 0.57 |
| $C_7F$ | 2.28 | 4.33 |
| $C_8F$ | 2.03 | 4.31 |
| Total alkyl fluorides | 21.45 | 28.05 |
| Acid Phase | | |
| HF wt. % pre-contact | 22.9 | 28.2 |
| HF wt. %* | 19.4 | 20.0 |

TABLE 2-continued

| | Run 1 | Run 2 |
|---|---|---|
| post contact HF wt. % reduction | 15.3 | 29.1 |

*via titration

The test results presented in Table 2 show that contacting a mixture representative of an alkylation re-run column bottoms stream, which contains HF, ASO, sulfolane and water, with an olefin containing hydrocarbon mixture results in significant production of alkyl fluorides with a corresponding significant reduction in wt. % HF in the HF containing mixture (ranging from 15.3 wt. % to 29.1 wt. % HF reduction).

EXAMPLE II

This example illustrates the effect of HF concentration on the efficiency of ASO recovery from an alkylation re-run column bottoms stream containing a mixture of HF, ASO, and sulfolane.

The following data set out in Table 3 were obtained from a commerical HF alkylation unit decanter.

TABLE 3

| Re-run column bottoms stream Component | Run 1 wt %. | Run 2 wt. % | Run 3 wt. % |
|---|---|---|---|
| Sulfolane | 60 | 60 | 60 |
| HF | 15 | 20 | 25 |
| ASO | 25 | 20 | 15 |
| Calculated ASO recovery, wt. % | 93.2 | 85.8 | 50.8 |

As can be seen from the data presented in Table 3, the wt. % ASO recovery increases significantly as the HF wt. % in the feed decreases.

Run 1, wherein the HF wt. % in the mixture was 15 wt. %, demonstrated an 8.6% increase in wt. % ASO recovery over Run 2, wherein the HF wt. % in the mixture was 20 wt. %.

Run 1, (15 wt. % HF) also demonstrated an 83% increase in wt. % ASO recovery over Run 3, wherein the HF wt. % in the mixture was 25 wt.

From the data in the Tables, it is readily apparent that the inventive method decreases the HF wt. % in an alkylation process system re-run column bottoms stream. This reduction in HF wt. % results in increased ASO recovery from a re-run column bottoms stream containing ASO and a volatility reducing additive.

Reasonable variations, modifications, and adaptations can be made within the scope of the disclosure and the appended claims without departing from the scope of this invention.

That which is claimed is:

1. A method for regenerating an alkylation catalyst mixture used in an alkylation process system, said method comprising the steps of:
    alkylating a first olefin with a first isoparaffin in the presence of said alkylation catalyst mixture comprising HF in an alkylation reaction zone thereby producing an alkylate product and an ASO reaction by-product;
    passing an alkylation reaction zone effluent comprising said alkylate product, said ASO reaction by-product and said alkylation catalyst mixture from said alkylation reaction zone to a separation zone for separating said alkylation reaction zone effluent into a hydrocarbon phase comprising said alkylate product, and an alkylation catalyst mixture phase comprising said alkylation catalyst mixture and said ASO reaction by-product;

passing at least a portion of said alkylation catalyst mixture phase to a re-run column for contact with an upwardly flowing gas stream comprising a second olefin and a second isoparaffin to provide a re-run column bottoms stream comprising at least a portion of said ASO reaction by-product, and a re-run column overhead stream comprising HF, at least a portion of said gas stream and an organic fluoride.

2. A method in accordance with claim 1 wherein said re-run column overhead stream is added to said alkylation reaction zone.

3. A method in accordance with claim 1 wherein said re-run column overhead stream is added to said separation zone.

4. A method in accordance with claim 1 wherein a portion of said first olefin is used as said second olefin.

5. A method in accordance with claim 1 wherein a portion of said first isoparaffin is used as said second isoparaffin.

6. A method in accordance with claim 1 wherein said re-run column overhead stream contains at least about 90 weight percent of the HF contained in said at least a portion of said alkylation catalyst mixture phase.

7. A method in accordance with claim 1 wherein said re-run column overhead stream contains at least about 95 weight percent of the HF contained in said at least a portion of said alkylation catalyst mixture phase.

8. A method in accordance with claim 1 wherein said re-run column overhead stream contains at least about 98 weight percent of the HF contained in said at least a portion of said alkylation catalyst mixture phase.

9. A method in accordance with claim 1 wherein the weight ratio of said second isoparaffin to said second olefin is in the range of from about 0.01 to about 100.

10. A method in accordance with claim 1 wherein the weight ratio of said second isoparaffin to said second olefin is in the range of from about 0.1 to about 10.

11. A method in accordance with claim 1 wherein the weight ratio of said second isoparaffin to said second olefin is in the range of from 0.25 to 5.

12. A method in accordance with claim 1 wherein said alkylation catalyst mixture further comprises a volatility reducing additive, and wherein said re-run column bottoms stream further comprises at least a portion of said volatility reducing additive.

13. A method in accordance with claim 12 further comprising:

separating said re-run column bottoms stream into an upper phase and a lower phase wherein said upper phase comprises a major portion of said at least a portion of said ASO reaction by-product and wherein said lower phase comprises a major portion of said at least a portion of said volatility reducing additive; and adding said lower phase to said alkylation reaction zone.

14. A method in accordance with claim 12 further comprising:

separating said re-run column bottoms stream into an upper phase and a lower phase wherein said upper phase comprises a major portion of said at least a portion of said ASO reaction by-product and wherein said lower phase comprises a major portion of said at least a portion of said volatility reducing additive; and adding said lower phase to said separation zone.

15. A method in accordance with claim 12 wherein said volatility reducing additive is a compound selected from the group consisting of sulfone, ammonia, methylamines, ethylamines, propylamines, butylamines, pentylamines, pyridine, alkylpyridines, melamine, hexamethylenetetramine, and combinations of any two or more thereof.

16. A method in accordance with claim 1 wherein said first isoparaffin is selected from the group consisting of isobutane, isopentane, and combinations thereof.

17. A method in accordance with claim 1 wherein said second isoparaffin is selected from the group consisting of isobutane, isopentane, and combinations thereof.

18. A method in accordance with claim 1 wherein said first isoparaffin is isobutane.

19. A method in accordance with claim 1 wherein said second isoparaffin is isobutane.

20. A method in accordance with claim 1 wherein said first olefin is selected from the group consisting of propylene, butene-1, isobutene, 2-butenes, methyl butenes, pentenes and combinations of any two or more thereof.

21. A method in accordance with claim 1 wherein said second olefin is selected from the group consisting of propylene, butene-1, isobutene, 2-butenes, methylbutenes, pentenes and combinations of any two or more thereof.

* * * * *